United States Patent
Marmor (10) Patent No.: US 10,265,046 B2
(45) Date of Patent: Apr. 23, 2019

(54) APPARATUS, SYSTEM AND METHODS FOR PROPER TRANSESOPHAGEAL ECHOCARDIOGRAPHY PROBE POSITIONING BY USING CAMERA FOR ULTRASOUND IMAGING

(71) Applicant: Visura Technologies, LLC, Evanston, IL (US)

(72) Inventor: David B. Marmor, Evanston, IL (US)

(73) Assignee: Visura Technologies, Inc., Minneapolis, MN (US)

( * ) Notice: Subject to any disclaimer, the term of this patent is extended or adjusted under 35 U.S.C. 154(b) by 337 days.

(21) Appl. No.: 14/952,289

(22) Filed: Nov. 25, 2015

(65) Prior Publication Data

US 2016/0150947 A1     Jun. 2, 2016

Related U.S. Application Data

(60) Provisional application No. 62/084,969, filed on Nov. 26, 2014.

(51) Int. Cl.
*A61B 1/00* (2006.01)
*A61B 8/12* (2006.01)
(Continued)

(52) U.S. Cl.
CPC ............ *A61B 8/12* (2013.01); *A61B 1/00045* (2013.01); *A61B 1/00103* (2013.01);
(Continued)

(58) Field of Classification Search
CPC .................. A61B 5/687; A61M 25/01; A61M 2039/1027
(Continued)

(56) References Cited

U.S. PATENT DOCUMENTS 1,761,761 A * 6/1930 Vicente .................. A61B 17/24
                                                                                                  606/108
3,877,429 A     4/1975 Rasumoff
(Continued)

FOREIGN PATENT DOCUMENTS

| WO | WO 2013/008106 | 1/2013 |
|----|----------------|--------|
| WO | WO 2014/113530 | 7/2014 |
| WO | WO 2016/086145 | 6/2016 |

OTHER PUBLICATIONS

International Search Report and Written Opinion for International Application No. PCT/US2015/062701, dated Feb. 18, 2016.
(Continued)

*Primary Examiner* — Timothy J Neal
*Assistant Examiner* — Jae Woo (57) ABSTRACT

An apparatus, system and methods that comprise adding a removable or detachable carrier containing a camera and illumination to a TEE probe, thereby allowing the user to view the placement of the probe and minimize or reduce the risk of esophageal and pharyngeal complications during the positioning of the TEE probe into the patient's esophagus. The reduction or minimization of complications occurs by allowing the cardiologist direct visualization of pharyngeal and esophageal structures during intubation. This device and procedure eliminate any "blind procedure", whereby direct visualization of the pharyngeal structures and esophagus present a possible solution to these mechanical complications. Once the TEE probe has been properly positioned in the esophagus, the carrier is removed from the esophagus. The removable or detachable camera of the present disclosure can be used in other industries.

10 Claims, 5 Drawing Sheets

(51) Int. Cl.
- *A61B 1/05* (2006.01)
- *A61B 1/06* (2006.01)
- *A61B 1/267* (2006.01)
- *A61B 1/273* (2006.01)
- *A61B 8/08* (2006.01)
- *A61B 8/00* (2006.01)

(52) U.S. Cl.
CPC ........... *A61B 1/053* (2013.01); *A61B 1/06* (2013.01); *A61B 1/0676* (2013.01); *A61B 1/0684* (2013.01); *A61B 1/267* (2013.01); *A61B 1/2733* (2013.01); *A61B 8/0883* (2013.01); *A61B 8/4455* (2013.01); *A61B 1/00016* (2013.01); *A61B 1/00018* (2013.01); *A61B 1/00142* (2013.01)

(58) Field of Classification Search
USPC .......... 600/104, 109, 112, 114; 606/108
See application file for complete search history.

(56) References Cited

U.S. PATENT DOCUMENTS

| | | | |
|---|---|---|---|
| 4,211,234 | A | 7/1980 | Fisher |
| 4,327,738 | A | 5/1982 | Green et al. |
| 4,567,882 | A | 2/1986 | Heller |
| 4,723,864 | A | 2/1988 | Umeda |
| 4,773,394 | A | 9/1988 | Reichstein et al. |
| 4,815,470 | A | 3/1989 | Curtis et al. |
| 5,251,025 | A | 10/1993 | Cooper et al. |
| 5,390,661 | A * | 2/1995 | Griffith ............. A61B 1/00154 600/114 |
| 5,400,771 | A * | 3/1995 | Pirak ............. A61B 1/042 128/200.26 |
| 5,598,846 | A | 2/1997 | Peszynski |
| 5,630,782 | A | 5/1997 | Adair |
| 5,682,199 | A | 10/1997 | Lankford |
| 5,735,792 | A | 4/1998 | Vanden Hoek et al. |
| 5,743,731 | A | 4/1998 | Lares et al. |
| 5,846,182 | A | 12/1998 | Wolcott |
| 5,906,578 | A | 5/1999 | Rajan et al. |
| 5,941,818 | A | 8/1999 | Hori et al. |
| 5,976,075 | A | 11/1999 | Beane et al. |
| 6,083,151 | A | 7/2000 | Renner et al. |
| 6,156,006 | A | 12/2000 | Brosens et al. |
| 6,162,170 | A | 12/2000 | Foley et al. |
| 6,211,904 | B1 | 8/2001 | Adair et al. |
| 6,275,255 | B1 | 8/2001 | Adair et al. |
| 6,520,907 | B1 | 2/2003 | Foley et al. |
| 6,527,704 | B1 | 3/2003 | Foley et al. |
| 6,540,668 | B1 | 4/2003 | Schulz et al. |
| 6,543,447 | B2 | 8/2003 | Pacey |
| 6,863,674 | B2 | 3/2005 | Kasahara et al. |
| 6,884,220 | B2 | 4/2005 | Aviv et al. |
| 7,670,282 | B2 | 3/2010 | Mathis |
| 7,814,912 | B2 | 10/2010 | George et al. |
| 7,819,817 | B2 * | 10/2010 | Rahn ............. A61B 5/01 600/549 |
| 7,927,272 | B2 | 4/2011 | Bayer et al. |
| 7,946,981 | B1 | 5/2011 | Cubb |
| 7,955,255 | B2 | 6/2011 | Boulais et al. |
| 8,172,758 | B2 | 5/2012 | Harhen |
| 8,360,064 | B2 | 1/2013 | Swann et al. |
| 8,416,291 | B2 | 4/2013 | Carrey et al. |
| 8,545,396 | B2 | 10/2013 | Cover et al. |
| 8,667,966 | B2 | 3/2014 | Koike |
| 8,771,173 | B2 | 7/2014 | Fonger et al. |
| 8,882,682 | B2 | 11/2014 | Qiu |
| 8,926,503 | B2 | 1/2015 | St. George et al. |
| 8,961,398 | B2 | 2/2015 | Makower et al. |
| 9,560,954 | B2 | 2/2017 | Jacobs et al. |
| 2002/0082477 | A1 | 6/2002 | Kim |
| 2002/0198583 | A1* | 12/2002 | Rock ............. A61N 1/0517 607/122 |
| 2003/0036681 | A1* | 2/2003 | Aviv ............. A61B 1/2733 600/129 |
| 2003/0120168 | A1 | 6/2003 | Atlee, III |
| 2003/0208107 | A1 | 11/2003 | Refael |
| 2004/0102804 | A1 | 5/2004 | Chin |
| 2004/0210105 | A1 | 10/2004 | Hale et al. |
| 2004/0215058 | A1* | 10/2004 | Zirps ............. A61B 1/0008 600/127 |
| 2005/0090712 | A1* | 4/2005 | Cubb ............. A61B 1/00073 600/120 |
| 2005/0119523 | A1 | 6/2005 | Starksen et al. |
| 2005/0273012 | A1 | 12/2005 | Aviv et al. |
| 2006/0149129 | A1 | 7/2006 | Watts et al. |
| 2006/0241476 | A1* | 10/2006 | Loubser ............. A61B 8/12 600/463 |
| 2006/0276693 | A1 | 12/2006 | Pacey |
| 2006/0281971 | A1 | 12/2006 | Sauer et al. |
| 2007/0083225 | A1 | 4/2007 | Kiser et al. |
| 2007/0135803 | A1 | 6/2007 | Belson |
| 2007/0137651 | A1* | 6/2007 | Glassenberg ......... A61M 16/04 128/207.15 |
| 2007/0175482 | A1* | 8/2007 | Kimmel ............. A61B 1/018 128/207.14 |
| 2007/0203517 | A1 | 8/2007 | Williams et al. |
| 2008/0255441 | A1* | 10/2008 | Hadani ............. A61B 1/00105 600/373 |
| 2008/0312507 | A1 | 12/2008 | Kim |
| 2008/0319350 | A1 | 12/2008 | Wallace et al. |
| 2011/0178372 | A1 | 7/2011 | Pacey et al. |
| 2011/0263983 | A1 | 10/2011 | Peszynski |
| 2013/0116652 | A1 | 5/2013 | Rotman et al. |
| 2013/0150710 | A1 | 6/2013 | Zentgraf et al. |
| 2013/0184571 | A1 | 7/2013 | Wilkening et al. |
| 2013/0317300 | A1 | 11/2013 | Berci et al. |
| 2014/0018668 | A1 | 1/2014 | Zheng et al. |
| 2014/0081080 | A1 | 3/2014 | Intoccia et al. |
| 2015/0320392 | A1 | 11/2015 | Missov et al. |
| 2016/0150947 | A1* | 6/2016 | Marmor ............. A61B 1/00045 600/110 |
| 2016/0262722 | A1 | 9/2016 | Marmor et al. |
| 2017/0258440 | A1 | 9/2017 | Marmor |
| 2018/0092625 | A1 | 4/2018 | Marmor et al. |

OTHER PUBLICATIONS

Extended European Search Report for European Application No. 15862735.6, dated Apr. 26, 2018, 10 pages.

Office Action for U.S. Appl. No. 15/164,538, dated Jan. 12, 2017, 8 pages.

Office Action for U.S. Appl. No. 15/164,538, dated Dec. 28, 2017, 13 pages.

Office Action for U.S. Appl. No. 15/164,538, dated Jun. 2, 2017, 10 pages.

Office Action for U.S. Appl. No. 15/834,878, dated Feb. 9, 2018, 17 pages.

Office Action for U.S. Appl. No. 15/834,878, dated Oct. 1, 2018, 21 pages.

* cited by examiner

APPARATUS, SYSTEM AND METHODS FOR PROPER TRANSESOPHAGEAL ECHOCARDIOGRAPHY PROBE POSITIONING BY USING CAMERA FOR ULTRASOUND IMAGING

FIELD OF THE INVENTION

The present disclosure relates generally to a Transesophageal Echocardiography Endoscopic Camera Assist Device (TEECAD) for adding direct visualization to Transesophageal Echocardiography intubation (TEE), without having to develop a completely new TEE probe nor without the need to revamp existing echocardiography machines. In particular, the present disclosure comprises an attachable TEECAD probe, which is configured to be attached to an existing TEE probe prior to intubation. The TEECAD probe contains a camera and a light source, which will feed into a video monitor and allow the user or practitioner to visualize the path of the TEE probe as it is inserted into the esophagus and moved into position for the procedure. The TEECAD probe would add minimal width or girth to the TEE probe, and would be completely detachable and easily retractable after successful intubation of the esophagus, while leaving the probe in the proper location.

BACKGROUND OF THE INVENTION

Echocardiography, is a diagnostic modality that utilizes a transducer to transmit ultrasound waves to the heart, which deflect or rebound off the structures of the heart. A computer converts the resulting waves and displays them on a screen as 2 dimensional, 3 dimensional, or doppler wave images, which allow assessment of cardiac structure and function. The majority of echocardiograms are obtained from a transthoracic approach (TTE), which generally gives an excellent assessment of left ventricular and valvular structure and function. Transesophageal echocardiography similarly takes echocardiographic pictures of the heart, but the images are obtained behind the heart from the esophagus, rather than across the chest wall. The TEE approach is advantageous over TTE's in many circumstances, most commonly for optimal imaging of heart valves, assessing for left atrial appendage thrombus, examination of intracardiac tumors, and assessment for intracardiac shunting.

The TEE procedure offers a much clearer image of certain heart structures versus a standard TTE. The TEE probe is comprised of a flexible endoscope with ultrasound transducer at the tip. The probe is inserted into the mouth and advanced into the esophagus. From the esophageal position, the ultrasound beam does not have to travel through the chest wall, and therefore offers a much clearer image of several key heart structures, especially the atria and valves, that may not be seen as clearly with a TTE. During the procedure, the cardiologist can rotate the endoscope and examine the heart from different angles.

An example of an optical TEE probe is disclosed in U.S. Pat. No. 6,884,220, titled Optical Transesophageal Echocardiography Probe (Aviv, et al.), where the proposed probe contains an optical imaging element, a suction channel, and a light channel for illumination, among other elements. The disclosure relates to an optical Transesophageal Echocardiography probe having an optical fiber bundle to allow real-time visualization of the structures that are transverse as the device is passed via the mouth into the esophagus, wherein the probe has a unique profile which allows passage into the esophagus with a minimum amount of trauma to the patient.

Another disclosure, U.S. Pat. No. 4,327,738, titled Endoscopic Method & Apparatus Including Ultrasonic B-Scan Imaging (Green, et al.), discloses an endoscopic method and apparatus for the simultaneous visual and ultrasonic imaging of internal body parts through the use of a probe insertable into a body cavity. The probe includes a rectilinear transducer array acoustically coupled to the body through a cylindrical focusing lens having an outer face that conforms to the probe contour. An optical illuminating and viewing system is provided for optically viewing internal body parts through the probe, which includes an objective lens and illuminating means adjacent the distal ends of the probe and the transducer array. A removable eyepiece at the housing is used for direct viewing by the operator while guiding the probe into desired position in the body cavity. Means also are provided for viewing the optical image by a video camera having an output connected to a monitor adjacent the ultrasonic image display. Consequently, both the optical and ultrasonic images are simultaneously displayable and viewable by the operator.

Another disclosure, U.S. Pat. No. 4,567,882, titled Method For Locating The Illuminated Tip Of An Endotracheal Tube (Heller), discloses a medical tube with a fiber optic light conductor extending lengthwise through the wall of the tube, with the conductor ending in a light emitting and redirecting terminus adjacent the tube's distal end. In the disclosure, light emitted laterally from the tip of the tube may be visually and externally observed through the body wall of the patient for accurately and quickly determining the anatomical location of that tip.

One of the disadvantages of the TEE procedure is that the cardiologist inserts the flexible endoscope without being able to see where the scope is going. The procedure is usually done by feel and experience, and although most of these procedures occur without problems, a small percentage of these procedures can result in oropharyngeal, esophageal, or gastric trauma, which can be catastrophic complications with high mortality rates. To the extent a camera or other device for viewing the procedure is used, the device must be modified from its original design, which can be expensive, or the new design might create a scope that is much larger in width or girth, making the procedure more uncomfortable for the patient.

Thus, there is a need for a camera and light source device or camera system and methods in which the camera system is configured to be attached to a TEE probe or scope and disconnected or detached from the probe once the transducer at the end of the scope has been placed in the proper position for the procedure. Once in the proper location, the camera system can be removed from the patient prior to the procedure. The present disclosure solves these and other disadvantages of the prior art.

SUMMARY OF THE INVENTION

The present disclosure solves the disadvantages of, and improves on, the prior art systems as described herein. The present disclosure pertains to a device, system and methods that comprise adding a removable or detachable camera to a TEE probe, for example, by using a carrier comprised of a proximal component, a mid-section lumen and a distal component, and in which the distal component is configured to removeably attach to the distal end of the TEE probe. The distal component houses a camera and light source or LED and associated wiring back to the proximal component through the mid-section lumen for connection to a video monitor to allow the practitioner to view the placement of the TEE probe in the patient, thereby minimizing or reducing the risk of esophageal and pharyngeal complications during the positioning of the TEE probe into the patient's esophagus. The reduction or minimization of complications occurs by allowing the cardiologist direct visualization of pharyngeal and esophageal structures during intubation. This device and procedure eliminates any "blind procedure", whereby direct visualization of the pharyngeal structures and esophagus present a possible solution to these mechanical complications. Once the TEE probe is properly located, the carrier can be removed from the TEE probe and extracted from the patient.

Currently, during a TEE procedure, the probe is positioned in the patient's esophagus, usually under conscious sedation and with local anesthetic applied to the oropharynx. Intubation of the esophagus is almost always done without imaging assistance, and is essentially a "blind" procedure, done by operator feel and assisted by the patient swallowing at the appropriate time. Reported complication rates are generally low, with the most catastrophic potential complication being perforation of the esophagus or damage to pharyngeal structures.

While the reported complication rates appear low, these rates are likely to change as the risk profile of patients undergoing TEE evolves, especially with the advancing age of patients undergoing TEE, which will almost certainly lead to an increase in TEE related complications, such as esophageal and pharyngeal perforation, and accidental tracheal intubation. Current advances in cardiology, most notably catheter based valve interventions for "inoperable" patients, are creating a sizeable pool of elderly, high risk patients who generally need screening TEE's to qualify for said procedures, as often also peri-procedural TEE's.

A device, system and methods that provide the above-noted advantages is the TEECAD, a Transesophageal Echocardiography Endoscopic Camera Assist Device, which offers a way to allow the cardiologist direct visualization for TEE intubation, without having to develop a completely new TEE probe or revamp existing echocardiography machines to accommodate the technology. As detailed herein, the TEECAD device comprises a carrier with a camera and light source device and system that is configured to be attached to, and when necessary, removed from, an existing probe. The carrier or attachment device can be further configured with wiring to transmit information to a video monitor, which may be separate from the echocardiography machine. The device can also be used with an eyepiece for the cardiologists to look into during the placement of the probe. An advantage to the TEECAD device is the minimal added width and/or girth on the TEE probe, and the device is configured to be detachable from the probe and easily retractable after successful intubation of the esophagus.

In the preferred embodiment, the TEECAD device would consist of a carrier comprising a proximal component, a mid-section lumen and a distal component, and in which the distal component is of a shape and form to removeably attach to a TEE probe. The proximal component would be configured as a handle for the practitioner to hold or as a clip to be attached to the proximal end of the TEE probe. The distal component is configured to house a camera and light source and allow the associated wiring for those items to snake back through the mid-section lumen and the proximal component for connection to a video chip, video monitor or image processor as understood by one having ordinary skill in the art.

This configuration allows the practitioner to view the placement of the TEE probe in the patient as the TEECAD device would be configured to feed video of the probe placement (in the esophagus) on a separate portable monitor, which can be placed near the device dependent on the operator's preference. The distal component would be configured to be held in place on the back end of the TEE probe and could be removed with the correct amount of axial tension, once the TEE probe was successfully located in the esophagus. Once detached from the TEE probe, the TEECAD device could be retracted and removed from the patient's esophagus.

In the preferred embodiment, the distal component would be configured to house the small video camera, lens, and light source, such as an LED. The internal wiring will comprise of a video feed wire, a power source for the camera and LED. A control handle at the end of the device would provide any needed controls for the video feed and for the LED. The camera can also be wireless, and the light source and camera may contain an internal power supply, to reduce the need for some or all of the wires.

The removable or detachable carrier and camera of the present disclosure can be used in other industries. For example, in the construction industry, a similar detachable device can be used to visualize the placement of wires in a wall, where the wires are left behind and the camera is detached from the wires and pulled back to the user.

Other objects and advantages of the present invention will become apparent to one having ordinary skill in the art after reading the specification in light of the drawing figures, however, the spirit and scope of the present invention should not be limited to the description of the embodiments contained herein. For example, electromagnetic straps or a detachable sleeve can be used instead of the preferred embodiment to attach the carrier to the TEE probe during intubation. The electromagnetic straps could be de-energized once the TEE probe was in the proper location for removal of the carrier. Further, a sleeve could be configured to encase the TEE probe. The sleeve can be detached and withdrawn from the patient after intubation has occurred.

DETAILED DESCRIPTION

The present disclosure is an apparatus, system and related methods pertaining to an attachable and detachable TEECAD or Transesophageal Echocardiography Endoscopic Camera Assist Device. The TEECAD device increases the functionality of currently existing probes by transmitting video information to a video monitor during the placement of the probe. The video information can be displayed on a video monitor, which may or may not be separate from the echocardiography machine. In particular, the display monitor used during the transesophageal echocardiography procedure, allows the practitioner or cardiologist to see or visualize the path of the TEE probe as it is inserted into the esophagus and moved into position for the TEE procedure. The TEECAD device has minimal circumference or girth and would not create an issue during intubation. Further, the TEACAD device is configured to be completely detachable, and easily retractable after a successful intubation of the esophagus, while leaving the TEE probe in place, as described in detail herein.

Figure 1:
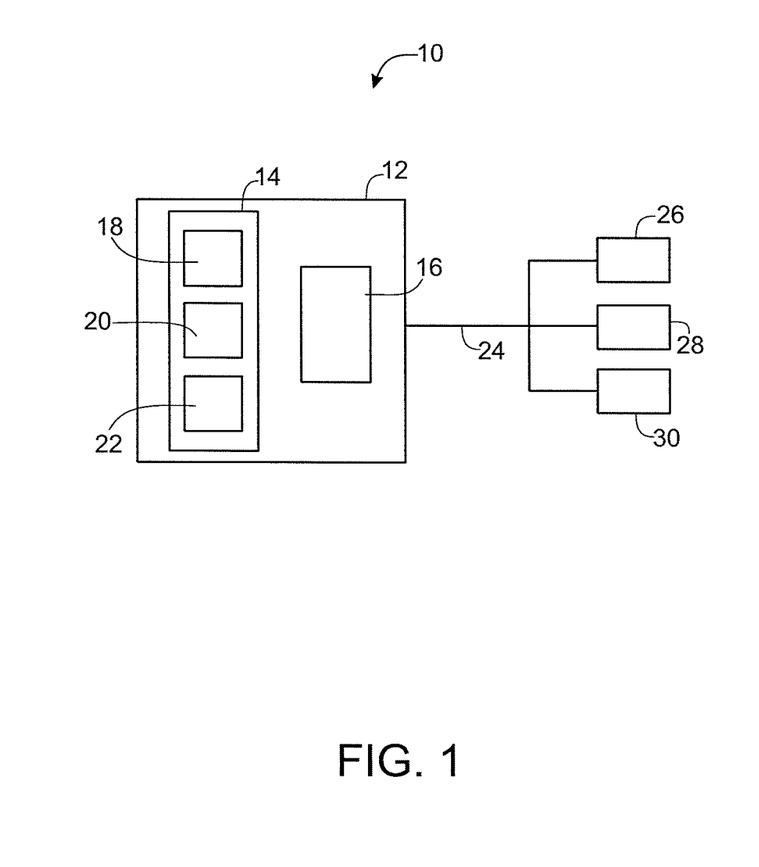
FIG. 1 is a functional block diagram view of an embodiment of a system for proper transesophageal echocardiography probe positioning by using a camera in accordance with the present disclosure.
Figure 2:
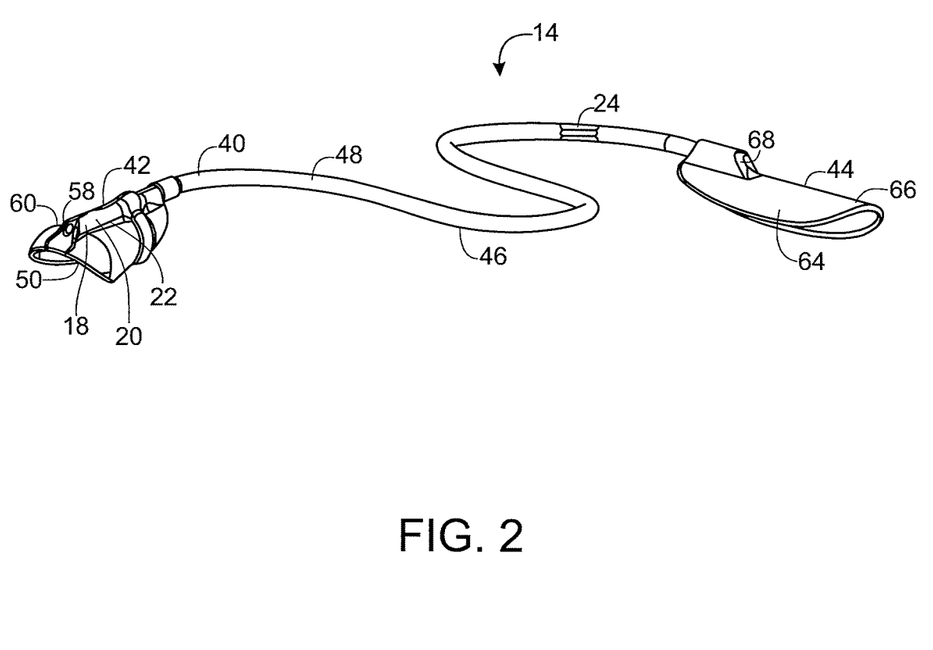
FIG. 2 illustrates an embodiment of an apparatus for proper transesophageal echocardiography probe positioning by using a camera in accordance with the present disclosure.

Referring to the drawings, wherein like reference numerals refer to the same or similar features in the various views, FIG. 1 is a functional block diagram view of an exemplary TEECAD system 10 which is used to assist in proper Transesophageal Echocardiography (TEE) probe positioning with the use of a detachable camera system in accordance with the present disclosure. The TEECAD system 10 comprises a TEECAD probe 12, which is combination of a TEECAD device 14, as shown in FIG. 2, and a TEE probe 16, for which the distal end is partially shown in FIG. 3, but which generally are about 80 cm in length. The TEECAD probe 12 also comprises, a lens 18, a camera 20, for a video feed, and a light source 22, such as an LED, along with the associated wiring 24 for the camera 20 and light source 22, along with any necessary controls 26 to control the camera 20, the light source 22, and any other devices or systems, as necessary.

As understood by one having ordinary skill in the art, the camera can be wireless, and the light source and camera may contain internal power supplies, thereby reducing the need for some or all of the wires. Further, the video feed from the camera 74 could be transmitted through the wire to a video monitor 30, which could be separate from the ultrasound display 28, although it is not required. The video monitor 30 can be placed near the device dependent on the cardiologist's preference, although the video feed can be transmitted remotely for access to viewing the procedure offsite or for educational purposes, among others In the preferred embodiment, the camera 20 is a NanEye 2D sensor by AWAIBA, which provides a system-on-chip camera head 20. The proprietary data interface technology permits cable length's up to 3 meters without any additional components at the distal end. Further, due to the low energy dissipation on the interface, no complicated shielding is required to meet EMC norms. Also, a small lens 18 can be assembled to the chip without increasing the total diameter of the sensor 20, making it one of the most compact digital cameras 20.

The exemplary TEECAD system 10 further comprises a display 28 for showing the ultrasonic results of the TEE probe 16 during a procedure, and a video monitor 30 for showing the video from the camera 20 as the TEECAD probe 12 is inserted into the esophagus and travels through the esophagus to the intended location. As described herein, the video monitor 30 allows the cardiologist to see the location of the TEECAD probe 12 as it travels through the patient's esophagus and as the TEECAD probe 12, and in particular the TEE probe 16, as it is moved into the proper location for the ultrasonic portion of the procedure. The monitor 30 and display 28 could be a single unit.

The present disclosure further contemplates that the camera 20 could send signals wirelessly to the monitor 30 or to a receiver (not shown) that could connect to a monitor 30, as understood by those having ordinary skill in the art. Further, as stated herein, the signals received from the camera could be transmitted remotely for teaching or analysis purposes.

FIG. 2 shows the preferred embodiment of the TEECAD device 14, which comprises a carrier 40. The carrier 40 comprises three separate components, a distal component 42, a proximal component 44 (both preferably molded components), and a mid-section lumen or retrieval tension member 46, preferably consisting of an extruded segment of polymer tubing 48. Although the carrier 40 comprises three separate components, any one or more of these components can be combined to perform the same function as described herein. For example, the mid-section lumen 46 and the proximal component 44 can be combined into an integral section and used with a non-integral distal component 42 to perform the same function as three separate components.

Figure 3:
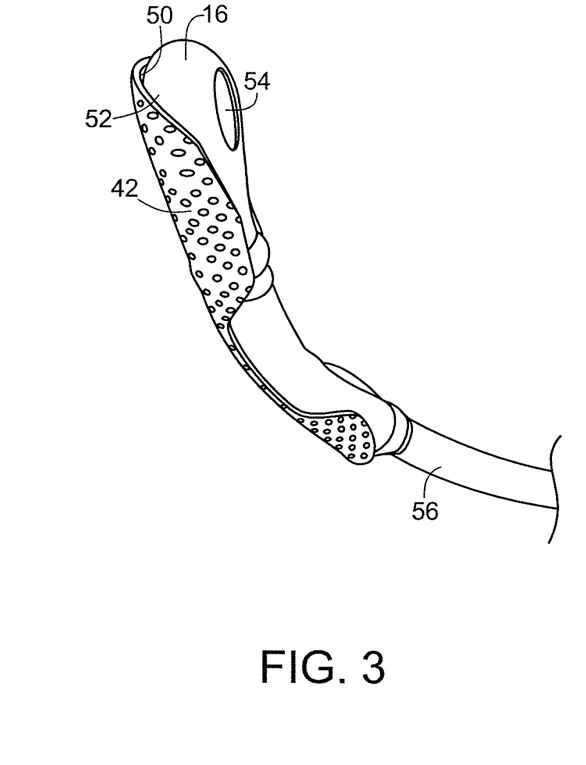
FIG. 3 illustrates an embodiment of an apparatus for proper transesophageal echocardiography probe positioning by using a camera in accordance with the present disclosure.

In the preferred embodiment, the distal component 42 comprises a concave section 50 configured to accept and support the distal portion of the TEE probe 16, and in particular, the distal component 42 is designed and configured to be removeably attached to and partially envelop the back side 52 of the TEE probe 16, opposite the ultrasound transducer 54, as shown in FIG. 3. The ultrasonic transducer 54 at the distal end is connected to the shaft 56 of the TEE probe 16. The shape and material of the distal component 42 of the carrier 40 shall be designed to provide sufficient mechanical stability to maintain communication with the back side 52 of the TEE probe 16 at the distal end, during TEACAD probe 12 intubation.

During the intubation procedure, while the TEE probe is inserted into the esophagus, the carrier will also be inserted into the esophagus. At least the distal component 42 and a portion of the mid-section lumen 46 will be inserted into the esophagus during intubation. The design and configuration of the distal component 42 of the carrier 40 shall allow the distal component 42, with minimal axial tension or pull, to detach from the back side 54 and distal end of the TEE probe 16, and to be retracted along the shaft 52 of the TEE probe 16 until the distal component 42 is effectively removed from the patient's esophagus, or removed to a distance that does not influence the TEE probe 16 performance. The distal component 42 of the carrier 40 can be attached to the back side 54 of the TEE probe 16 in a number of ways, as long as it can be detached after the TEE probe has been properly located, and removed from the patient.

As also shown in FIG. 2, contained within the distal component 42 of the carrier 40 will be an aperture 58 in which the camera 20, lens 18 and light source 22 will be located. The camera 20 will have coincident illumination 22 (built in), or in an alternative embodiment, an aperture in which only a camera 20 will be located and which will receive ancillary illumination 22 from a source not coincident to the camera 20. The ancillary illumination 22 may be located adjacent to the aperture 58 or be contained within the distal component 42. The built in lens 18 of the camera 20 and the illumination 22 will be arranged at the furthest most segment 60 of the distal component 42.

Although the preferred embodiment comprises a camera 20 and light source or LED 22 built directly into the carrier 40, an alternative embodiment comprises a separate camera sheath (not shown) which comprises the camera 20, the light source 22, and the associated wiring 24, that inserts through the mid-section lumen 46 of the carrier 40. In this embodiment, the camera sheath can be reused, while the carrier 40 is discarded after use.

FIG. 2 also shows the mid-section lumen 46 of the carrier 40, which in the preferred embodiment, which will run alongside the shaft 56 of the TEE probe 16 during intubation. The mid-section lumen 46 will have a smaller diameter, approximately 5 to 6 mm in diameter, than the shaft 52 of the probe 16. However, the mid-section lumen 46 shall be sufficiently thick to withstand the tensile force required to detach and withdraw the distal component 42 from the back end 54 of the TEE probe 16 and about the TEE probe shaft 52. The inside of the lumen 46 shall be sized and configured such that it shall contain the wiring 24 for the digital camera 20, or in some embodiments, the digital camera 20 and the illumination mechanism 22. In some embodiments, the lumen 46 shall be reinforced such that the cross-section of the lumen 46 may be minimized, but which still can provide adequate tensile force, such that the distal component 42 may be retracted safely and effectively.

The proximal component 44 of the carrier 40 comprises a handle or clip 64 that is configured to be removeably attached to the proximal component 44 of the TEE probe 16. Although it is not necessary that the proximal component 46 attach to the TEE probe 16, the handle or clip 64 may partly or fully encircle the proximal component 44, if it does. The proximal component 44 may attach and, if a clip, be removed with a spring mechanism 66. Either way, the proximal component 44 will be configured with an opening 68 to accommodate the wiring 24 for the camera 20 and LED 22.

The carrier 40, which is constructed of the three components, the distal component 42, the lumen 46, and the proximal component 44, shall be continuous, and constructed such that the components may be attached to each other by conventional methods of cold vulcanization as well as using heat or solvent bonding, as understood by one having ordinary skill in the art.

The camera component in the preferred embodiment, such as the NanEye 2D sensor by AWAIBA, shall include a video chip, LED lighting, and a clear polymer lens covering the assembly. Although the NanEye 2D is the preferred embodiment, the LED lighting may also be a separate component from the camera embodiment, and possibly integrated directly into distal component 42 of the carrier 40. Regardless, the digital camera 20 and illumination system 22 shall attach to an image processor (if necessary) and viewing monitor 30 which is located proximal to but not integral to the carrier 40.

The present disclosure contemplates other embodiments in which a carrier similar that described herein can be attached to a TEE probe 16 and, as such, a TEACAD probe 12 can be inserted into the esophagus. Once the TEE probe 16 is properly positioned (as viewed in the monitor 30), the distal component 42 or equivalent of the carrier can be removed from the distal portion of the TEE probe 16 opposite the ultrasonic transducer 54 and the TEECAD device 14 can then be removed or withdrawn from the esophagus.

The present disclosure contemplates that the entire carrier 40, along with the camera 20 and light source 22, can be disposable once used, or the camera 20 and light source 22 can be reused as described herein. Whether the entire device is discarded or a portion is reused will depend on the overall cost and the possibility of sterilizing any part of the device after each use. In particular, the carrier 40, which is the least expensive item, will be disposable. However, the camera 20 and light source 22 may or may not be reusable. The camera 20 and LED 22 may be incorporated directly into the carrier 40 if they are to be disposed of after use. If the camera 20 and LED 22 are to be sterilized and reused, then a separate thin camera sheath (not shown) containing the camera 20 and the LED or light source 22, can be thread through the lumen 46 of the carrier 40, and then removed, sterilized or disinfected, and reused.

Figure 4:
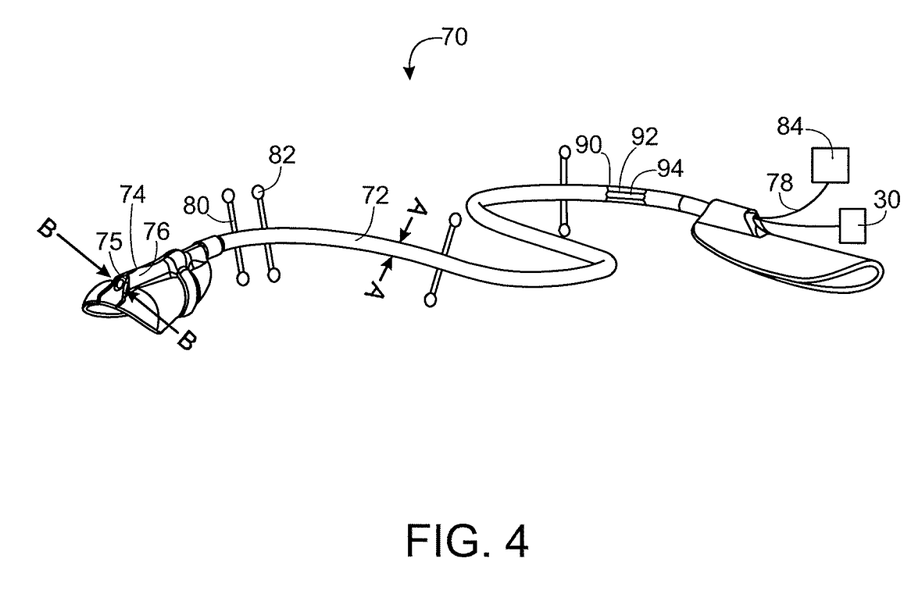
FIG. 4 illustrates an alternative embodiment of an apparatus for proper transesophageal echocardiography probe positioning by using a camera in accordance with the present disclosure.

FIG. 4 shows an alternative embodiment of the present disclosure. In the alternative embodiment, a TEECAD device 70 comprises a shaft 72, which contains within the wires or cabling for a camera 74, light 76 and control wires 78. The shaft 72 is a thin, mini-endoscope or lumen, which contains the wiring or cabling, and which would be attached to a standard TEE probe 16 during intubation. The shaft 72 comprises adjustable straps 80 that would be configured to secure the TEECAD device 70 to the TEE probe 16.

In the embodiment, the straps 80 would be held in place with small electromagnets 82 that could be activated and deactivated from controls 84. In doing so, the electromagnets 82 could be energized to attach the TEECAD device 70 to the TEE probe 16 prior to insertion into the esophagus. As before, the combination of the TEE probe 16 with the attached TEECAD device 70 creates a TEECAD probe 12. Once the TEECAD probe 12 is successfully located in the proper position in the esophagus for ultrasonic imaging, the electromagnets 82 could be de-energized, thereby allowing the TEECAD device 70 to detach from the TEE probe 16, and be extracted from the patient's esophagus.

Figure 5:
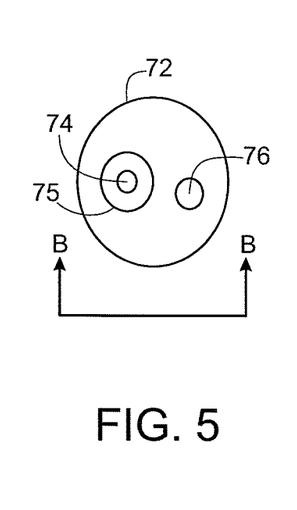
FIG. 5 illustrates an alternative embodiment of a system for proper transesophageal echocardiography probe positioning by using a camera in accordance with the present disclosure.

In an embodiment, there would be four straps 80, two near the distal end for stability of the camera 74, and two attached to the middle area of the shaft 72 of the TEECAD device 70. The straps 80 would be thin, and have rounded edges, to assure minimal trauma to the esophagus during intubation and removal of the TEECAD device 70. As shown in FIG. 5, cross-sectional view B-B, the distal end of the TEECAD device 70 would comprise a small video camera 74, a lens 75, and an light source or LED 76.

Figure 6:
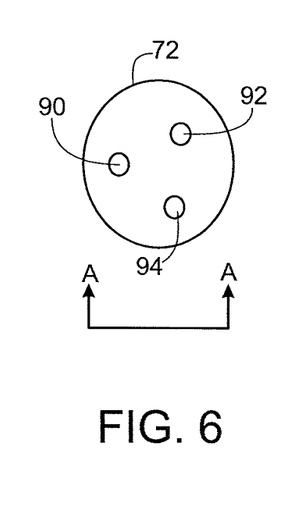
FIG. 6 illustrates an alternative embodiment of a system for proper transesophageal echocardiography probe positioning by using a camera in accordance with the present disclosure.

As shown in FIG. 6, cross-sectional view A-A, the internal wiring in the shaft 72 comprises a video feed wire 90 from the camera 74 to the monitor 30, a power source 92 for the light source or LED 76, and a power line 94 for the control wires 78, to control the energizing and de-energizing of the electromagnets 82 on the straps 80. The controls 84 at the end of the TEECAD device 70 would provide the controls for the video feed 74, LED 76, and ability to activate and deactivate the electromagnets 82 on the straps 80. As understood by one having ordinary skill in the art, the camera can be wireless, and the light source may contain an internal power supply, and the electromagnets may be controlled remotely, to reduce the need for some or all of the wires, similar to all of the embodiments herein.

Similar to the discussion above, the video feed from the camera 74 could be transmitted through the wire to a video monitor 30, which could be separate from the ultrasound display 28, although it is not required. The video monitor 30 can be placed near the device dependent on the cardiologist's preference, although the video feed can be transmitted remotely for access to viewing offsite or for educational purposes, among others.

In accordance with the alternative embodiment, by using the straps 80 and energizing the electromagnets 82 with the controls 78, the shaft 72 of the TEECAD device 70, with the integral camera 74 and lights 76, can be attached to the TEE probe 16. The resulting TEECAD probe 12 can be inserted into the esophagus to reduce or minimize the risk of esophageal and pharyngeal complications, by allowing the cardiologist to directly visualize the pharyngeal and esophageal structures on the video monitor 30 during intubation. Once the TEECAD probe 12 has been properly inserted into the esophagus, the electromagnets 82 can be de-energized using the controls 84, thereby allowing the TEECAD device 70 to detach from the TEE probe 16, so that the TEECAD device 70 can be removed from the patient and the ultrasonic imaging on the display 28 can take place.

In an alternative embodiment, the TEECAD device can be a detachable sleeve, used instead of the electromagnetic straps 80. The sleeve could be configured to encase the TEE probe 16 and an endoscope and be detached and withdrawn from the patient after intubation has occurred.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

Although a number of embodiments have been described above with a certain degree of particularity, those skilled in the art could make numerous alterations to the disclosed embodiments without departing from the spirit or scope of this disclosure. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. As used herein, the phrased "configured to," "configured for," and similar phrases indicate that the subject device, apparatus, or system is designed and/or constructed (e.g., through appropriate hardware, software, and/or components) to fulfill one or more specific object purposes, not that the subject device, apparatus, or system is merely capable of performing the object purpose. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method of using a camera for adding visualization of a patient's esophagus during Transesophageal Echocardiography intubation, the steps comprising:
   prior to intubation, removeably attaching the camera to a distal portion of a transesophageal echocardiography (TEE) ultrasound probe;
   intubating the patient with the TEE ultrasound probe with the camera removeably attached to the distal portion of the TEE ultrasound probe;
   viewing images of the intubation captured by the camera from outside the patient during the intubating; and
   with the distal portion of the TEE ultrasound probe disposed in a proper position for capturing ultrasound images of a heart, detaching the camera from the distal portion of the TEE ultrasound probe by withdrawing the camera proximally along a body portion of the TEE ultrasound probe and to a position outside the patient, the withdrawing the camera proximally including applying a proximal force to a retrieval tension member, the retrieval tension member defining a lumen having a diameter smaller than a diameter of the TEE ultrasound probe.

2. The method of claim 1, wherein the retrieval tension member is formed at least in part of extruded polymer tubing.

3. A method for assisting intubation of a transesophageal echocardiography (TEE) ultrasound probe with a proximal portion and a distal portion and an ultrasound transducer disposed at the distal portion, comprising:
   inserting the distal portion of the TEE ultrasound probe having releasably coupled thereto a camera into an oral cavity of a patient;
   viewing, after the inserting, a display of image data of an esophagus of the patient captured by the camera,
   while viewing the display of image data, and with the camera releasably coupled to the distal portion of the TEE ultrasound probe, advancing distally the distal portion of the TEE ultrasound probe through the esophagus; and with both the distal portion of the TEE ultrasound probe and the camera disposed together within the esophagus, applying tension proximally to a retrieval tension member to remove the camera from the patient via the esophagus while leaving the TEE ultrasound probe ultrasound disposed in a proper position within the esophagus for capturing ultrasound images of a heart of the patient, the retrieval tension member defining a lumen having a diameter smaller than a diameter of the TEE ultrasound probe.

4. The method of claim 3, wherein the retrieval tension member is formed at least in part of extruded polymer tubing.

5. The method of claim 3, wherein the camera is releasably attached to the distal portion of the TEE ultrasound probe via a coupling member, the coupling member defining a concave portion, the distal portion of the TEE ultrasound probe being disposed within the concave portion of the coupling member during the inserting.

6. The method of claim 3, wherein the advancing includes applying a distal force to a proximal portion of the TEE ultrasound probe that is disposed outside the patient.

7. A method for assisting intubation of a transesophageal echocardiography (TEE) ultrasound probe, comprising:

inserting a distal portion of a TEE ultrasound probe having releasably coupled thereto an camera into an oral cavity of a patient, the camera configured to capture image data of an esophagus of the patient when disposed therein;

after the inserting, viewing a display of image data of the esophagus captured by the camera;

while viewing the display of image data, and with the camera releasably coupled to the TEE ultrasound probe, maneuvering distally within the esophagus the distal portion of the TEE ultrasound program to dispose an ultrasound transducer of the TEE ultrasound probe in a proper position for capturing ultrasound images of a heart;

with both the distal portion of the TEE ultrasound probe and the camera releasably attached to the distal portion of the TEE ultrasound probe disposed within the esophagus such that the ultrasound transducer is disposed in the proper position, applying a proximal force to a retrieval tension member to cause sliding of the camera proximally along a body of the TEE ultrasound probe and away from the distal portion of the TEE ultrasound probe, the retrieval tension member defining a lumen having a diameter smaller than a diameter of the TEE ultrasound probe; and removing, after the sliding, via the esophagus, and with the TEE ultrasound probe disposed at least in part within the esophagus, the camera from the patient.

8. The method of claim 7, wherein the retrieval tension member extends through the esophagus and out the oral cavity of the patient when the camera is releasably attached to the distal portion of the TEE ultrasound probe and both the camera and the probe are disposed within the esophagus.

9. The method of claim 8, wherein the retrieval tension member is formed at least in part of extruded polymer tubing.

10. The method of claim 8, wherein the camera is releasably attached to the distal portion of the TEE ultrasound probe via a coupling member, the coupling member defining a concave portion, the distal portion of the TEE ultrasound probe being disposed within the concave portion of the coupling member during the inserting.

* * * * *